(12) United States Patent
Rivlin et al.

(10) Patent No.: US 10,758,396 B2
(45) Date of Patent: Sep. 1, 2020

(54) 3D PRINTED SPLINT AND CAST

(71) Applicant: Dimension Orthotics, LLC, Philadelphia, PA (US)

(72) Inventors: Michael Rivlin, Philadelphia, PA (US); Pedro Beredjiklian, Philadelphia, PA (US); Alexander R. Vaccaro, Philadelphia, PA (US); Michael J. Sileski, Philadelphia, PA (US); Emilia Pollnow, Philadelphia, PA (US); Mary Grace Maggiano, Philadelphia, PA (US); Cynthia Watkins, Philadelphia, PA (US)

(73) Assignee: Dimension Orthotics, LLC, Philadelphia, PA (US)

( * ) Notice: Subject to any disclaimer, the term of this patent is extended or adjusted under 35 U.S.C. 154(b) by 559 days.

(21) Appl. No.: 15/418,033

(22) Filed: Jan. 27, 2017

(65) Prior Publication Data
US 2017/0216078 A1 Aug. 3, 2017

Related U.S. Application Data

(60) Provisional application No. 62/288,172, filed on Jan. 28, 2016.

(51) Int. Cl.
*A61F 5/00* (2006.01)
*A61F 5/058* (2006.01)

(52) U.S. Cl.
CPC ................ *A61F 5/05866* (2013.01)

(58) Field of Classification Search
CPC .. A61F 5/00; A61F 5/01; A61F 5/0102; A61F 5/0104; A61F 5/013; A61F 5/0118;
(Continued)

(56) References Cited

U.S. PATENT DOCUMENTS 4,161,175 A * 7/1979 Bentele ............... A61F 5/05875
602/6
5,556,373 A 9/1996 Motloch
(Continued)

OTHER PUBLICATIONS

Quigley, E., A few ways to strengthen 3D printed parts, Oct. 10, 2014, 3ders.org, pp. 1-19 (Year: 2014).*
(Continued)

*Primary Examiner* — Kim M Lewis
(74) *Attorney, Agent, or Firm* — Panitch Schwarze Belisario & Nadel LLP

(57) ABSTRACT

A 3D printed cast or splint for application to a patient's body to immobilize a body part includes first and second shell portions configured to conform to at least a portion of the body part. The first shell portion has a distal end, a proximal end, opposing interfacing edges, a plurality of venting holes and a first engagement mechanism positioned proximate one of the opposing interfacing edges. A reinforcement portion extends between the proximal and distal ends. The second shell portion has a distal end, a proximal end, opposing interfacing edges, a plurality of venting holes and a second engagement mechanism positioned proximate one of the opposing interfacing edges. The first engagement mechanism interacts with the second engagement mechanism in a mounted configuration to facilitate mounting of the first shell portion to the second shell portion.

12 Claims, 10 Drawing Sheets

(58) Field of Classification Search
CPC .... A61F 5/04; A61F 5/05; A61F 5/058; A61F 5/05841; A61F 5/0585; A61F 5/05858; A61F 5/05866; A61F 5/05875; A61F 2005/0158; A61F 2005/0172; A61F 2240/00; A61F 2240/001; A61F 2240/002
USPC .................................. 602/16, 5–12; 700/118
See application file for complete search history.

(56) References Cited

U.S. PATENT DOCUMENTS

| | | | |
|---|---|---|---|
| 6,725,118 | B1 | 4/2004 | Fried et al. |
| 2005/0015172 | A1 | 1/2005 | Fried et al. |
| 2005/0080369 | A1* | 4/2005 | Kim .................. A61F 5/05858 602/12 |
| 2011/0301520 | A1 | 12/2011 | Summit et al. |
| 2016/0074203 | A1 | 3/2016 | Hall |
| 2017/0224520 | A1* | 8/2017 | Karasahin ............ A61B 5/1116 |

OTHER PUBLICATIONS

Karasahin, Deniz, Osteoid Medical cast, attachable bone stimulator, 2014, A'Design Award & Competition, pp. 1-4 (Year: 2014).*

Milionis, A., Noyes, C., Loth, E., and Bayer, I.S., Superhydrophobic 3D Printed Surfaces by Dip-Coating, 2014, NSTI-Nanotech 2014, vol. 2, pp. 157-160 (Year: 2014).*

3DXTech Advanced Materials, Carbon Fiber ABS and PLA Test Data, Apr. 8, 2015, 3DXTech Advanced Materials Blog, pp. 1-3 (Year: 2015).*

Paterson, A.M., Donnison, E., Bibb, R.J., and Campbell, I.R., Computer-aided design to support fabrication of wrist splints using 3D printing: A feasibility study, 2014, Hand Therapy, vol. 19(4), pp. 102-113 (Year: 2014).*

Active Armor, downloaded from web page: http://activarmor.com/, Download date May 2017, original posting date: unknown, 2 pages.

Xkelet Easy Life, downloaded from web page:https://www.xkelet.com/?lang=en>, 2017, Download date: May 2017, original date: unknown, 8 pages.

MHOX, 2012, downloaded from web page: http://mhoxdesign.com, Download date: May 2017, original posting dtae: unknown, 1 page.

Exovite, 2015, downloaded from web page: exovite.com <http://exovite.com, Download date: May 2017, original posting date: unknown, 2 pages.

3D Printing Industry,The Authority on 3D Printing, downloaded from web page: https://3dprintingindustry.com/about-us/ , Download date: May 2017, original posting date unknown, 4 pages.

Zdavprint: New 3D Printed Casts for Bone Healing, 3D Printing Pin,Feb. 2015, downloaded from web page: http://www.3dprintingpin.com/zdavprint-new-3d-printed-casts/, original posting date 2013, 5 pages.

Cortex, Evill, 2013, downloaded from web page : http://www.evilldesign.com/cortex, Download date: May 2017, Original posting date 2013, 12 pages.

* cited by examiner

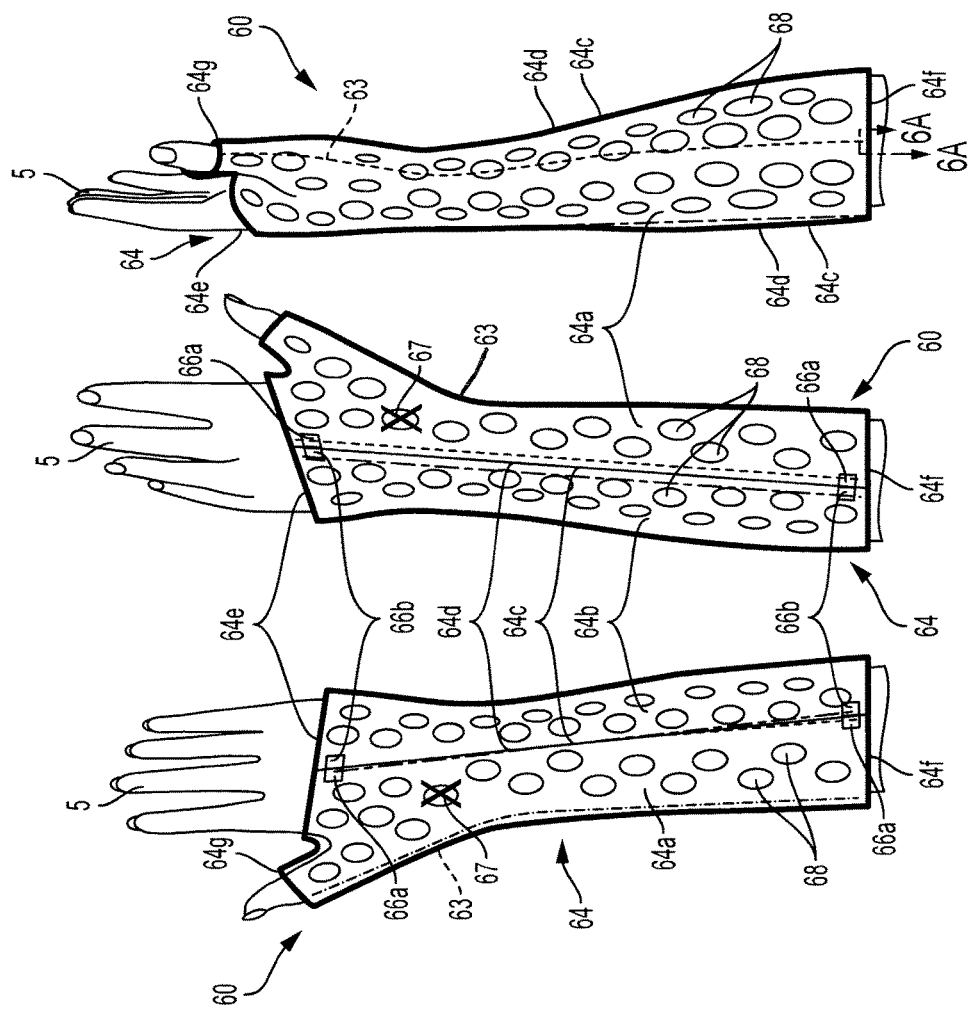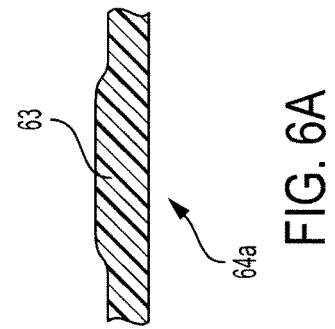

3D PRINTED SPLINT AND CAST

CROSS REFERENCE TO RELATED APPLICATIONS

This application claims priority to U.S. Provisional Patent Application No. 62/288,172, filed on Jan. 28, 2016, entitled "3D Printed Polymer Coated Splint and Cast," the contents of which are incorporated herein by reference.

BACKGROUND OF THE INVENTION

Rigid casts or splints that are applied and formed directly to a patient's body to immobilize the body part and promote healing are known. Problems with rigid casts and splints include time consuming and complicated, inconsistent constructions, limitations in sizing the rigid cast or splint to a specific patient's anatomy, limited breathability, limited waterproof or water resistant options, irritability to the patient's skin, inability to adapt the rigid cast or splint to a patient's healing, therapy or changes in swelling around the impacted area, one-time nature of the rigid cast or splint that is destroyed at the conclusion of healing, limited adaptability to provide strength, stiffness or flexibility at selected areas to promote healing and limited strength and stiffness. When a patient wears a cast or splint, the size of their limb may change due to atrophy, swelling, or reduced swelling. The patient's limb may also change due to healing of the skin around the injury or as the result of being enclosed in a traditional cast or splint for extended periods of time. When these changes occur, the cast irritates the user's skin and this may be pronounced in particular sections of the casting where the original formation did not match the patient's anatomy. The conventional casts or splints are also not adaptable to a patient's injury or condition and are typically constructed by skilled technicians. It is desirable to design, produce and deploy a splint or cast that overcomes the deficiencies of these conventional casts and splints.

BRIEF SUMMARY OF THE INVENTION

The preferred present invention is directed to a three-dimensional ("3D") printed, polymer coated splint or cast. Benefits of 3D orthosis fabrication include, but are not limited to, custom fit, adaptability, breathability, rapid production, and affordable material. The orthosis can also be designed to accommodate personalization such as a patient's name or even a corporate logo on the surface of the orthosis. Furthermore, the innovative construction and simple uniform design allows for immobilization in a waterproof and washable orthosis that can withstand the elements, allow for sport participation, and fit in shirts, gloves, and other garments for a seamless wear. Coating the relatively stiff and custom formed base cast with an inert polymeric material, such as silicone, limits skin reactions when compared to conventional casts and their known materials. The inert polymeric material preferably does not interact chemically with any wound associated with the patient's condition, such as open skin wounds and associated scarring. The coating and base cast are preferably non-absorbent. The inert polymeric material also does not traumatize the wound or surrounding skin, is relatively flexible to accommodate swelling or other changes to the patient's anatomy and, therefore, generally does not interfere with wound healing. The inert polymeric coating on the custom formed base cast has also been found to promote healing, particularly as a therapy for scar management, burn hypertrophic scars and minor keloids.

Briefly stated, the preferred present invention is also directed to a cast or splint for application to a patient's body to immobilize a body part. The cast includes a relatively stiff base cast configured for custom forming to the body part and an inert polymeric coating adhered to the external surface of the base cast. The base cast is constructed of a relatively stiff material that is adaptable to 3D printing.

In another aspect, the preferred invention is directed to a 3D printed cast or splint for application to a patient's body to immobilize a body part. The 3D printed cast includes first and second shell portions configured to conform to at least a portion of the body part. The first shell portion has a distal end, a proximal end, opposing interfacing edges, a plurality of venting holes and a first engagement mechanism positioned proximate one of the opposing interfacing edges. A reinforcement portion extends between the proximal and distal ends. The second shell portion has a distal end, a proximal end, opposing interfacing edges, a plurality of venting holes and a second engagement mechanism positioned proximate one of the opposing interfacing edges. The first engagement mechanism interacts with the second engagement mechanism in a mounted configuration to facilitate mounting of the first shell portion to the second shell portion. The first and second shell portions may also be utilized independently and attached to the patient's impacted body part with a securing mechanism, such as straps.

In a further aspect, the preferred invention is directed to 3D printed cast or splint for application to a patient's body to immobilize a body part of the patient's body. The 3D printed cast or splint includes a first shell portion and a second shell portion. The first and second shell portions are constructed of a substantially rigid material and are configured to conform to at least a portion of the body part. The first shell portion has a distal end, a proximal end, opposing interfacing edges, a plurality of venting holes and a first engagement mechanism positioned proximate one of the opposing interfacing edges. A bone stimulation port is positioned between the proximal and distal ends of the first shell portion. The second shell portion is constructed of the substantially rigid material. The second shell portion includes a distal end, a proximal end, opposing interfacing edges, a plurality of venting holes and a second engagement mechanism positioned proximate one of the opposing interfacing edges of the second shell portion. The first engagement mechanism interacts with the second engagement mechanism in a mounted configuration to secure the first shell portion to the second shell portion. The interfacing edges of the first and second shell portions are positioned adjacent to each other in the mounted configuration

BRIEF DESCRIPTION OF THE SEVERAL VIEWS OF THE DRAWINGS

The foregoing summary, as well as the following detailed description of the preferred invention, will be better understood when read in conjunction with the appended drawings. For the purpose of illustrating the preferred 3D printed splint or cast, there are shown in the drawings embodiments which are presently preferred. It should be understood, however, that the invention is not limited to the precise arrangements and instrumentalities shown. In the drawings:

FIG. 6 comprises top and bottom plan views and a side elevational view of a 3D printed base cast in accordance with a sixth preferred embodiment of the present invention created from the digitized base cast of FIG. 2A;

FIG. 6A is a cross-sectional view of a reinforcement portion of the base cast of FIG. 6, taken along line 6A-6A of FIG. 6;

DETAILED DESCRIPTION OF THE INVENTION

Figure 1:
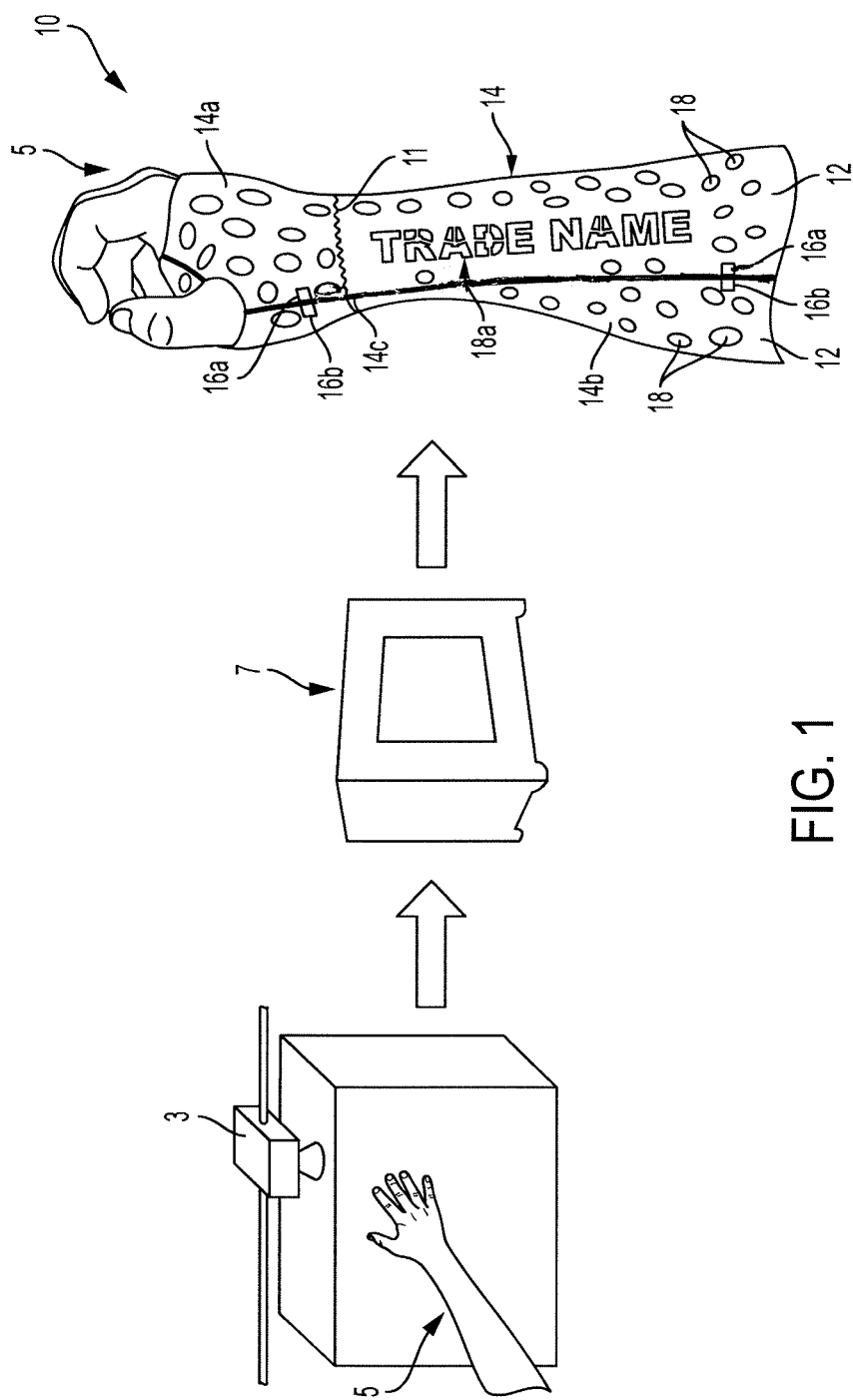
FIG. 1 is a series of images related to the construction of a 3D printed base cast in accordance with a first preferred embodiment of the present invention.

Certain terminology is used in the following description for convenience only and is not limiting. Unless specifically set forth herein, the terms "a", "an" and "the" are not limited to one element but instead should be read as meaning "at least one". The words "right," "left," "lower," and "upper" designate directions in the drawings to which reference is made. The words "inwardly" or "distally" and "outwardly" or "proximally" refer to directions toward and away from, respectively, the patient's body, or the geometric center of the preferred 3D printed splint or cast and related parts thereof. The words, "cast," "brace," and "splint" are utilized substantially interchangeably herein, such that cast generally means splint herein and splint generally means cast, particularly with respect to the preferred methods and constructions of the preferred cast or splint. The words, "anterior", "posterior", "superior," "inferior", "lateral," "radial," "medial," and related words and/or phrases designate preferred positions, directions and/or orientations in the human body to which reference is made and are not meant to be limiting. The words "cast," "splint," "orthosis," and "brace" are substantially utilized interchangeably herein and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1-9, a patient with an orthopaedic injury or other pathology may require treatment with a splint (not circumferential) or a cast (circumferential) as a form of immobilization. The patient has their body part, such as wrist, hand, fingers, ankle, foot, leg, forearm, torso, neck, hip, back or combinations of these body parts, digitized. After image processing, a 3D printed, custom, waterproof cast or splint, generally designed 10, 20, 30, 40, 50, 60, 70, 80, 90, is applied to the patient with a custom and form fit. The 3D printed casts or splints 10, 20, 30, 40, 50, 60, 70, 80, 90 of the preferred embodiments described herein are generally water resistant, form fit, adaptable, personalized to the individual patient and configured specifically for the patient's particular injury to promote healing, therapy and at least visual access to the patient's skin proximate the injury.

Figure 1A:
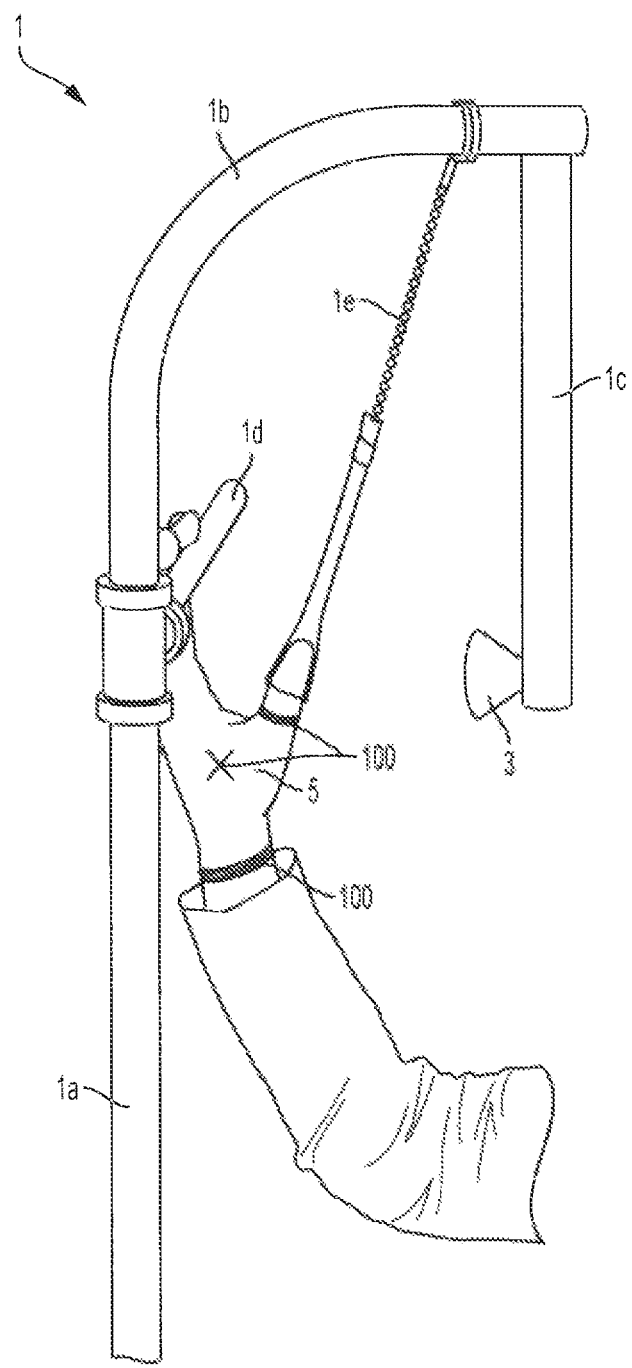
FIG. 1A is a front perspective view of a scanning stand that may be utilized in the process of constructing the 3D printed base cast in accordance with the preferred present invention.
Figure 2A:
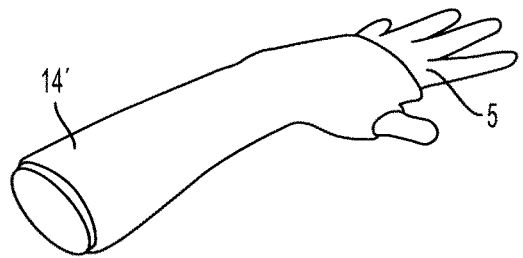
FIG. 2A is a top perspective view of a digitized base cast mounted to a patient's virtual arm in accordance with preferred embodiments of the present invention

Referring to FIGS. 1-2A, in a first preferred embodiment, the cast or splint 10 preferably includes a first shell portion 14a, a second shell portion 14b that comprise a base cast or splint 14. The first and second shell portions 14a, 14b of the first preferred embodiment preferably include a coating 12 applied to exposed surfaces. The first preferred embodiment is not limited to including the coating 12 and the base cast or splint 14 may be mounted to the patient's body part to immobilize or limit motion a joint in a mounted configuration (FIG. 1A). The coating 12 may alternatively only be applied to surfaces of the base cast or splint 14 facing the patient's skin for additional protection of the skin to limit irritation or treatment of wounds. The coating 12 may be constructed of a breathable material. The coating 12 is preferably comprised of an inert polymeric material, such as silicone, which has preferred properties for direct contact with the patient's skin, particularly when placed on scars to promote skin healing. The coating 12 is not limited to silicone coatings and may be comprised of any material that may be adhered to the first and second shell portions 14a, 14b, withstand the normal operating conditions of the cast or splint 10 and is able to take on the size and shape of the preferred coating 12. In addition, the inert polymeric coating 12 is preferably flexible to accommodate changes to the patient's anatomy, such as swelling or reduction of swelling to maintain the relative form and custom fit around and on the patient's body part 5 for a limited period of time after application of the cast 10 to the body part 5, such as at least six to eight (6-8) weeks. The coating 12 is also not limited to inert polymeric materials or to specifically polymeric materials. The coating 12 may be comprised of nearly any material applied to the base cast 14 in nearly any manner that is able to take on the general size and shape of the coating 12, withstand the normal operating conditions of the coating 12 and perform the described, preferred functions of the coating 12. For example, the coating 12 may be comprised of a non-polymeric material that is applied to the base cast 14 to promote healing of a body part 5 to which the cast or splint 10 is applied. In addition, the cast or splint 10 may be constructed and deployed as only the base cast 14 without the coating 12, such as for temporary immobilization while the patient is assessed or temporarily immobilized for subsequent treatment.

New developments in 3D printing technologies offer multiple possible new frontiers to improve patient care, satisfaction, and offer potential financial and investment opportunities. In the preferred embodiments of the present invention, the patient has 3D mapping, digitalization and templating performed of an injured body part 5, such as a wrist and forearm 5, and using custom imaging software, a form fitting customized cast or splint 10, 20, 30, 40, 50, 60, 70, 80, 90 such as the first preferred cast or splint 10, is fabricated within minutes to fit the body part 5. After mapping, digitalization and templating, the base cast or splint 14 is preferably formed or printed by a 3D image processor and printer 7. The base cast or splint 14 may be formed as a single part, a pair of shell portions 14a, 14b or multiple portions that are assembled together to define the base cast or splint 14 that fits to the body part 5. This 3D scanning, mapping, manipulating and printing process is described generally with respect to the first preferred cast or splint 10, but is equally applicable to the below-described additional preferred casts or splints, 20, 30, 40 50, 60, 70, 80, 90.

In the first preferred embodiment, the base cast 14 is constructed of an assembly including the first shell portion 14a and the second shell portion 14b that are selectively and removably connected to each other. The first shell portion 14a may form to an upper part of the patient's body part 5 and the second shell portion 14 may form to a lower part of the patient's body part 5, but are not so limited and may be designed and configured in nearly any manner such that the assembled base cast 14 is able to form fit around the body part 5 and substantially immobilize the body part 5 and, preferably, a joint associated with the body part 5, such as the wrist. The first and second shell portions 14a, 14b may be selectively connectable to each other by adhesive bonding, fasteners, clips, hook and loop material or nearly any other fastening mechanisms or techniques that are able to secure the first and second shell portions 14a, 14b relative to each other and around the body part 5. The first and second shell portions 14a, 14b may also be formed and configured with engagement features, such as tongue and groove features integrally formed with the first and second shell portions 14a, 14b during the 3D printing process that snap into each other and around the body part 5, such as the patient's hand, wrist and forearm, without the use of bulky straps or padding. The printed base cast or splint 14 of the first preferred cast or splint 10 is preferably covered by the skin-friendly inert polymer coating 12, which conforms to the skin and minimizes unevenness of the fabricated and assembled base cast 14. Through the use of 3D imaging software, the base cast 14 can be modeled with specifications for the correction of an orthopedic deformity, to compensate for swelling or irregularity of the patient's body part 5, as well as offer customization. The base cast 14 may also be configured with interchangeable swelling zones that accommodate swelling of different portions or sections of the body part 5. The interchangeable swelling zones may be comprised of flexible materials printed into the base cast 14, flex areas 11, ratcheting or movable first and second engagement mechanisms 16a, 16b or other features that accommodate swelling of the body part 5. The first and second engagement mechanisms 16a, 16b may be configured to change color or otherwise provide a visual indication if they have been opened or tampered with after being locked together in the mounted configuration, may be associated with a key, potential for use by a parent of a juvenile patient to permit removal of the base cast 14 for predetermined periods and replacement of the base cast 14 or may be configured as a tamper proof mechanism. The first and second engagement mechanisms 16a, 16b may also be associated with flex areas 11 that accommodate flexing of the first shell portion 14a and second shell portion 14b relative to each other to accommodate swelling, deformity or comfort for the patient. The base cast 14 may also include flex areas 11 to provide physical therapy opportunities for the patient. For example, the base cast 14 may include a flex area 11 in the palmar region to allow for flexor digitorum profundus compression ("FDPC") for composite digit flexion and functional hand use.

Benefits of 3D base cast 14 fabrications include, but are not limited to, custom fit, breathability, and affordable material. The base cast 14 can be designed to accommodate personalization, through formation of a symbol on or in the base cast 14. The base cast 14 may, for example, include a plurality of venting holes 18 therein to create breathability to the patient's skin. The venting holes 18 can be configured in nearly any manner and configuration, such as having different sizes and shapes. The venting holes 18 may be configured as symbols 18a, taking on user or designer preferred shapes and sizes, such as hearts, a patient's name, a corporate logo, a trade name, sports team logos, use and care instructions, reminders, and other symbols desirable for the patient, physician or designer. The venting holes 18 may also be designed and configured for clinical purposes, such as having openings over patient scarring for visual inspection of healing, application of medication, exposure of an injection site, relief for bony prominences, or for similar clinical purposes. One of the venting holes 18 may be configured for positioning over the styloid process of the wrist. Furthermore, the innovative construction and design preferably allows for immobilization in a waterproof and washable inert polymeric coated cast or splint 10 that can withstand the elements, allow for sports participation, and fit in shirts, gloves, and other garments for a seamless wear. The preferred coated cast 10 of the first preferred embodiment is generally water-resistant as a result of the preferred silicone coating 12 over the generally rigid, resilient base cast 14, such that the patient may continue relatively normal activities, even swimming and related sporting activities and everyday activities, such as showering and general hygiene.

Referring to FIGS. 1-2A, in the first preferred construction, the impacted body part 5, such as the patient's hand, wrist and forearm are digitized and templated and a virtual base cast or digitized base cast 14' (FIG. 2A) is preferably designed based on the size and shape of the body part 5, as well as the knowledge and experience of the physician and designer. The body part 5 is preferably digitized and templated with a visual digitization mechanism 3 that visually scans the body part 5 and produces a 3D image of the body part 5, such as the digitized base cast 14'. The digitization mechanism 3 may also be comprised of a mechanical mechanism that selects and records points or areas of the body part 5 to create the 3D image or the digitized base cast 14'. The base cast 14 may be designed with the plurality of venting holes 18 having various sizes and shapes of the first preferred embodiment or, such as the variously sized heart-shaped venting holes 28 of the second preferred embodiment, as is shown in FIGS. 2B-2D and will be described below. The first preferred base cast 14 may also be formed as an assembly, including the first shell portion 14*a* and the second shell portion 14*b*. The first shell portion 14*a* preferably includes a first engagement mechanism 16*a* proximate an interfacing edge 14*c* of the first shell portion 14*a* and a second engagement mechanism 16*b* proximate an interfacing edge 14*c* of the second shell portion 14*b*. The first and second engagement mechanisms 16*a*, 16*b* preferably include snap-fit features or holes therein that accept fasteners to secure the first and second portions 14*a*, 14*b* together around the body part 5 in a mounted configuration. The first and second shell portions 14*a*, 14*b* are not limited to inclusion of the first and second engagement mechanisms 16*a*, 16*b* or to inclusion of any specific fastening mechanism or technique, as long as the first and second shell portions 14*a*, 14*b* may be engaged to each other in the mounted configuration around the body part 5 to substantially immobilize the body part 5 or a joint, such as the wrist, of the body part 5 to promote healing.

In the first preferred embodiment, the polymeric coated cast 10 may include flex areas 11, such as at the patient's wrist or other movable joint of the body part 5 where the flex area 11 will be placed proximate the joint in the mounted configuration. The flex areas 11 may be formed into the base cast 14 at preferred locations or areas to allow for limited motion of the body part 5 at the flex areas 11 and the flex area 11 may be configured such that motion of the body part 5 is limited to a specific direction or over a predetermined angle of motion. For example, the base cast 14 may be formed with a relatively flexible material at the flex area 11 or may be designed with an hinge, living hinge, thinned material, more flexible material or other mechanism or technique at the flex areas 11 that permit movement of the body part 5 in the mounted configuration to limit damage or stiffening of the body part 5 when the preferred splint or cast 10 is mounted thereto. The coated splint or cast 10 of the first preferred embodiment is not limited to inclusion of the flex areas 11 and the flex areas 11 may not be included in certain embodiments of the coated cast or splint 10 without significantly impacting the broad inventive concept.

The polymeric coated cast 10 of the first preferred embodiment may also be designed and configured with expanding buffer zones that allow for swelling of the body part 5. For example, the base cast 14 may be configured with spacing between its inner surface and the patient's skin at the body part 5 that accommodates swelling and other changes to the body part 5. The polymeric coated cast 10 may also be configured with relatively soft, thick and pliable coatings 12 on an inner portion thereof that also accommodates swelling or changes in configuration of the body part 5 in the mounted configuration. The first and second shell portions 14*a*, 14*b* may also be configured with ratcheting or tightening first and second engagement mechanisms 16*a*, 16*b* such that the first and second shell portions 14*a*, 14*b* may be spaced from each other in an initial mounted configuration when the body part 5 is swelled and the ratcheting or tightening first and second engagement mechanisms 16*a*, 16*b* may be tightened after swelling is mitigated such that the first and second shell portions 14*a*, 14*b* are drawn closer together and closer around the body part 5 as swelling reduces. The first and second engagement mechanisms 16*a*, 16*b* may alternatively be configured to bias the first and second shell portions 14*a*, 14*b* toward each other any apply a predetermined amount of force to the body part 5 such that the first and second shell portions 14*a*, 14*b* are automatically drawn toward each other as the swelling of the body part 5 is reduced.

The polymeric coated cast or splint 10 of the first preferred embodiment may further be designed during the virtual cast application and 3D printing process for slow manipulation or alignment of a deformity or fracture displacement by fracture angle calculation (on X-rays) of the body part 5. Software may be utilized with the visual digitization mechanism 3, the 3D printer 7 or a central computing device (not shown) to calculate serial casting requirements to multi-cast treatment of deformity or malalignment. The central computer device may further include capability to import a radiograph or other image of the body part 5 and overlay the image onto the scanned body part 5 for modelling the digitized base cast 14' and defining the base cast 14. The polymeric coated cast 10 may be applied for a predetermined amount of time to the body part 5, removed and a second polymeric coated cast 10 subsequently be applied to the body part 5 to conduct further slow manipulation or further alignment of the deformity of the body part 5. Such manipulation and alignment may be planned and applied utilizing the initial digitized base cast 14' and templating of the body part 5 by designing progressively different sized and shaped base casts 14 to facilitate the slow manipulation and alignment of the body part 5, as desired and planned by the physician. For example, the designer can easily manipulate the initial digitized base cast 14' to apply corrective pressures and forces to the body part 5 and manufacture progressively corrective base casts or splints 14' that may be printed by a 3D printer 7 and mailed to the patient, thereby limiting inconvenience to the patient of travelling to the care provider, as deemed appropriate by the physician.

The preferred polymeric coated cast or splint 10 of the first preferred embodiment may also be constructed with transparent/translucent materials for the base cast 14 and the coating 12 that allows visualization of the patient's body part 5 and skin through the coated cast 10. The transparent base cast 14 may be utilized specifically for visualization of the patients skin for wound treatment of monitoring, such as for burns. The plurality of venting holes 18 may also be designed and configured for visualization of particular areas of the body part 5 and skin or for clinical purposes, as was described in further detail above.

The first preferred polymeric coated cast 10 may be designed and configured with the first and second shell portions 14*a*, 14*b* that snap together into the mounted configuration (FIG. 1) around the body part 5. The first and second shell portions 14*a*, 14*b* may be snapped or secured together with the first and second engagement mechanisms 16*a*, 16*b*. The first and second engagement mechanisms 16*a*, 16*b* may be comprised of nearly any fastening or securement mechanism or technique for positioning the first and second shell portions 14*a*, 14*b* in the mounted configuration. The first and second shell portions 14a, 14b may alternatively be adhesively bonded together such that the polymeric coated cast 10 is not removable from the body part 5 without damaging or cutting the first preferred cast or splint 10. In the first preferred embodiment, the interfacing edges 14c may be masked during the inert polymeric coating 12 application process such that the interfacing edges 14c are not coated to permit a tight fit between the first and second portions 14a, 14b along the interfacing edges 14c. The interfacing edges 14c are not limited to being masked during the coating 12 application process and the interfacing edges 14c may be coated with the coating 12, without significantly impacting the performance of the coated cast 10 of the first preferred embodiment.

The base cast 14, including each of the first and second shell portions 14a, 14b, of the first preferred embodiment may be designed and constructed of numerous materials that provide a relatively strong and stiff configuration for the coated cast or splint 10 and is able to withstand the normal operating conditions of the base cast 14. The base cast 14 may be constructed of various materials and combinations of materials, such as polycarbonate, polyether ether ketone ("PEEK"), a powder polymeric material, acrylonitrile butadiene styrene ("ABS"), polylactic acid ("PLA"), a biocompatible thermoplastic, a composite carbon material and carbon reinforced composite materials, as well as similar material. In the first preferred embodiment, the material of the base cast 14 is preferably a biocompatible, light-weight, rigid material that accepts application of the coating 12 thereon. These materials may be utilized for any of the below-described base casts 14, 24, 34, 44, 54, 64, 74, 84, 94 in nearly any combination.

The coating 12 is preferably applied to external surfaces of the base cast 14 to form the coated base cast 10, including surfaces proximate the patient's skin in the mounted configuration and surfaces spaced from the patient's skin. The base cast 14 is not limited to having all surfaces coated with the coating 12, such as masking the interfacing surfaces 14c, as was described above, or only applying the coating 12 to predetermined surfaces of the base cast 14. In addition, various thicknesses of the coating 12 may be applied to specific sections or areas of the base cast 14 and different types of coatings 12 may be applied or 3D printed onto the base cast or splint 14 in specific sections or areas of the base cast 14. The inner surfaces of the base cast 14 may, for example, be coated or printed with the coating 12 that includes medicament infused therein for treatment of the body part 5 and the patient's skin, a different coating 12 may be applied to the surfaces of the base cast 14 facing away from the body part 5 that harden or has variable colors and designs based on user preferences and alternative coatings 12 may otherwise be applied to the base cast 14 for ornamental or clinical purposes. In the first preferred embodiment, the coating 12 is comprised of silicone and has a substantially uniform application to the external surfaces of the base cast 14.

In the preferred process for constructing the custom polymeric coated cast or splint 10 of the first preferred embodiment, the patient's impacted body part 5 is fully digitized to be splinted or casted utilizing the visual digitization mechanism 3. The body part 5 is preferably processed by a software algorithm to define an appropriate base cast 14 that preferably accounts for the deformity/correction, spacing between the base cast 14 and the body part 5 and the added layer of coating 12 that is applied to the surfaces of the base cast 14. The base cast 14 is preferably processed by the software algorithm by defining the digitized base cast 14'. The base cast 14 is then printed on the 3D printer 7 with a calculated fill pattern or the venting holes 18 (lattice structure or holes and internal material fill is variable based on specific need of rigidity). The base cast 14 may also be virtually created through use of software associated with the visual digitization mechanism 3, the 3D printer 7 or a central computing device to create an optimal cast or splint 10 with calculated areas of strain/stress based on injury patter, size of the cast or splint 10, anatomy of the body part 5 and required treatment course. The software is preferably able to calculate padding, if required, need for reinforcement, areas where reinforcement is not required, internal fill of the material of the base cast 14, patterns for the venting holes 18 and other related features. The coating 12 may also be printed on the 3D printer 7. The final processed virtual cast or splint 14 is then printed on the 3D printer 7 with the substantially rigid material, such as reinforced carbon fiber infused plastic. The 3D printer 7 may be comprised of a single or multiple head printer to print only a single material or multiple types of materials for construction of the base cast 14 and its related components. The 3D printer 7 may utilize continuous liquid interface production to construct the base cast 14. The materials and methods utilized with the 3D printer 7 may also result in isotropic or anisotropic materials incorporated into the base cast 14. The base cast 14 may alternatively and subsequently be coated with the inert polymeric material, such as silicone, and the coated cast or splint 10 is applied to the patient's body part 5 in the mounted configuration. The cast or splint 10 is preferably mounted to the body part 5 by clamping the body part between the first and second shell portions 14a, 14b and locking or securing the shell portions 14a, 14b together utilizing the first and second engagement mechanisms 16a, 16b. The first preferred cast or splint 10 includes several first and second engagement mechanisms 16a, 16b along the interfacing edges 14c to secure the shell portions 14a, 14b together along the entire length of the cast or splint 10.

Referring to FIG. 1A, the patient's body part 5 may be positioned and stabilized with a scanning stand 1. The preferred scanning stand 1 includes a base post 1a, a lateral post 1b and a scanning post 1c. The scanning stand 1 further includes a grasping bar 1d that the patient preferably grasps with their fingers and a thumb positioning mechanism 1e for positioning the patient's thumb that extends from the lateral post 1b. The scanning stand 1 is designed and configured to facilitate consistent scanning of the patient's arm 5 with the visual digitization mechanism 3. In operation, the user places there body part 5 in a relatively consistent position from patient to patient relative to the scanning stand 1 and the visual digitization mechanism 3 rotates around the body part 5 to produce the 3D scan of the body part 5. The system creates the digitized base cast 14' from the scan and the 3D printer 7 prints the base cast 14 based on the scan. The scanning stand 1 is not required for operation of the preferred system and method, but is preferred for stabilizing patient's arm 5 during the scanning step to improve consistency and accuracy of the scan using the visual digitization mechanism 3. The system, for example, may operate without the scanning stand 1 by having a technician scan the body part 5 with a hand-held visual digitization mechanism 3 to define the digitized base cast 14'. The system may also be configured to have the patient utilize the visual digitization mechanism 3 to scan their own body part 5 and assist in designing the digitized base cast 14' and the base cast 14. The patient may be able to determine colors, type of symbol 18a present on the base cast 14 and other features, based on user preferences. The patient may utilize a tablet computer with a visual digitization mechanism 3 integrated therein and software may be loaded onto the tablet computer to guide the patient through design of the preferred cast or splint 10. The software may include a library of available selections for the patient to select for production of the customized cast or splint 10.

The scanning stand 1 may also be utilized with a calibration body part (not shown) that has known dimensions. The calibration body part may be scanned with the visual digitization mechanism 3 and compared to a previous scan of the calibration body part. The visual digitization mechanism 3 may subsequently be recalibrated to the know scan of the calibration body part in a manner that would be apparent to one having ordinary skill in the art based on a review of the present disclosure.

The scanning stand 1 and visual digitization mechanism 3 may also be used with marking tape, marking indicators or scanning marks 100 that are applied to the body part 5. The marking tape 100 provides a visual indication to the visual digitization mechanism 3 of features of the digitized base cast 10'. The marking tape 100 may be applied directly to the body part 5 to locate edges or ends of the digitized base cast 14' and the base cast 14, locations for the venting holes 18, locations for the logo 18a, locations for the interfacing edges 14c, locations for the flex areas 11, locations for the first and second engagement mechanisms 16a, 16b, locations for the reinforcement portions 53, locations for the bone stimulation port 57, locations for added padding or coating over prominences or areas of concern, markings for a targeted pathology or treatment zone and other features of any of the preferred casts or splints 10, 20, 30, 40, 50, 60, 70, 80, 90 described herein. The marking tape 100 is preferably comprised of a material that may be applied to the body part 5 that may be detected by the visual digitization mechanism 3 to indicate a feature of the digitized base cast 14' or the base cast 14. The marking tape 100 may alternatively be comprised of a mesh glove, boot or sleeve (not shown) that is worn by the patient on the body part 5 during the scanning process to provide a relatively consistent scan using the visual digitization mechanism 3. The preferred systems are not limited to utilizing the marking tape 100 and may include software associated with the visual digitization mechanism 3, the printer 7 or other components of the system that are able to manipulate the size, shape and configuration of the digitized base cast 14' or the base cast 14, the weight, flexibility, rigidity, venting hole 18 locations and sizes, interfacing edge 14c locations and other features of the base cast 14.

Multiple prototypes of the coated cast or splint 10 for mounting to specific scanned arms in multiple materials that are 3D printed have been produced. The preferred prototypes of the coated casts 10 have been constructed of silicone covering base casts 14 using spray, submersion and applied silicone coverage. Various materials may be utilized in constructing the coated cast 10 and its component parts, including plaster, fiberglass, thermoplastic, PEEK, PEEK powder, FDA approved Nylon, carbon fiber infused polylactic acid ("PLA") and related materials that may be 3D printed utilizing the 3D printer 7. The base cast 14 may have nearly any configuration that is able to substantially immobilize the body part 5 to a range of motion preferred by the physician. The base cast 14, for example, may be constructed as a solid body, include patterned vent holes 8, such as hexagonal honeycomb or may have contoured surface features that result in a shape or patterns following application of the coating 12, such as symbols, designs, company names, trade names or company logos 18a. An example the company logo 18a or symbol designed as a portion of the plurality of vent holes 18 is shown in FIG. 1. The symbol 18a may be integrated into the base cast 14, may be imprinted on the surface of the base cast 14 or coating 12 via colors or may be imprinted with texture on the surface of the base cast 14 during the printing process. In addition, the base cast 14 or coating 12 may be colored or include symbols 18a or representations desired by the patient or physician. Further, the base cast 14 or coating 12 may include instructions or warnings on external surfaces for the benefit of the patient. The base cast 14 or coating 12 may also include or integrate glow in the dark materials for illumination, particularly when the cast or splint 10 is configured as a splint 10 that is selectively removed from the body part 5 such that the glow in the dark material makes the splint 10 relatively simple to find in dark environments. The base cast 14 or coating 12 may also include reflective strips for sports or for safety purposes for runners, hikers or walkers in nighttime or dark environments.

The coating 12 may be applied in various manners to the base cast 14, such as by coating, printing, applying, adding, dipping, spraying, lining, painting or other techniques that adhere the coating 12 to the surfaces of the base cast 14. In addition, the surfaces of the base cast 14 that are desired to include the coating 12 thereon may be treated or pre-conditioned to specifically enhance adhesion of the coating 12 to the base cast 14. Alternatively, the portions of the base cast 14 that do not require or to which application of the coating 12 is not desired, may be treated or pre-conditioned, such as by masking, to substantially prevent the coating 12 from adhering to the conditioned portions of the base cast 14. The coating 12 may be applied to the base cast 14 having various colors and textures or may change colors based on patient mood or biometric features, such as temperature or other metrics and other data, such as the time the base cast 14 is worn by the patient.

Figure 2B:
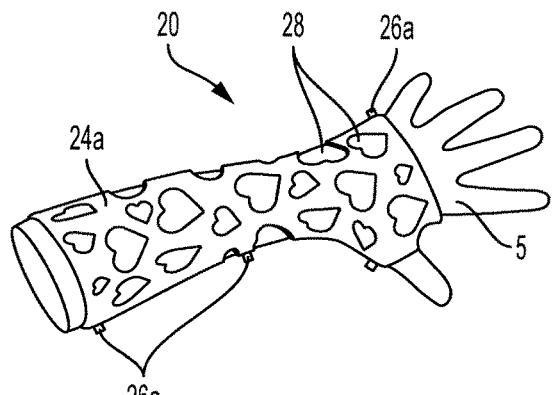
FIG. 2B is a top perspective view of a first portion of a 3D printed based cast in accordance with a second preferred embodiment of the present invention, created from the digitized base cast of FIG. 2A, wherein the first portion is mounted to a patient's arm.
Figure 2C:
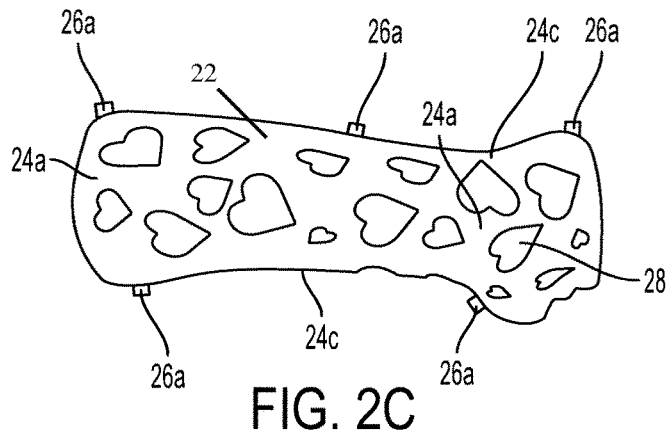
FIG. 2C is a top plan view of the first portion of FIG. 2B.
Figure 2D:
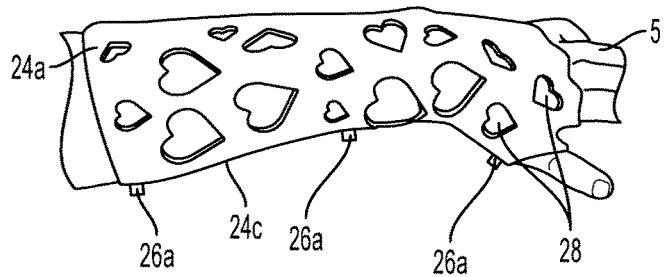
FIG. 2D is top perspective view of the 3D printed base cast created from the digitized base cast of FIG. 2A, wherein the base cast is mounted to the patient's arm.

Referring to FIGS. 2B-2D, a second preferred cast or splint 20 has a similar construction compared to the first preferred cast or splint 10 and like reference numbers are utilized to identify like features of the second preferred cast or splint 20 with a number "2" prefix replacing the "1" prefix to distinguish the features of the cast or splint 10 of the first preferred embodiment from the cast or splint 20 of the second preferred embodiment.

The second preferred cast or splint 20 includes ornamental or decorative shaped venting holes 28, for example, the heart-shaped plurality of venting hole 28. The plurality of venting holes 28 are not limited to having the heart-shape and may have nearly any shape preferred by the user or designer that results in the second preferred cast or splint 20 having sufficient structural strength and stiffness to withstand the normal operating conditions of the cast or splint 20 and perform the preferred functions of the cast or splint 20. The preferred first shell portion 24a also includes five first engagement mechanisms 26a with three on a first interfacing edge 24c and two on the opposing second interfacing edge 24c. The first engagement mechanisms 26a of the second preferred embodiment are comprised of bosses that mate with opposing second engagement mechanisms (not shown) of the second shell portion (not shown). The first and second engagement mechanisms 26a may be locked or tied together with fasteners, clips, clamps, integrated zip ties, ratcheting mechanisms, releasable locking mechanisms, elastic bands or other fastening or engagement features. The second preferred splint or cast 20 is also not coated with the coating, but is not so limited and may include the coating 12 described above of the first preferred embodiment.

Figure 3A:
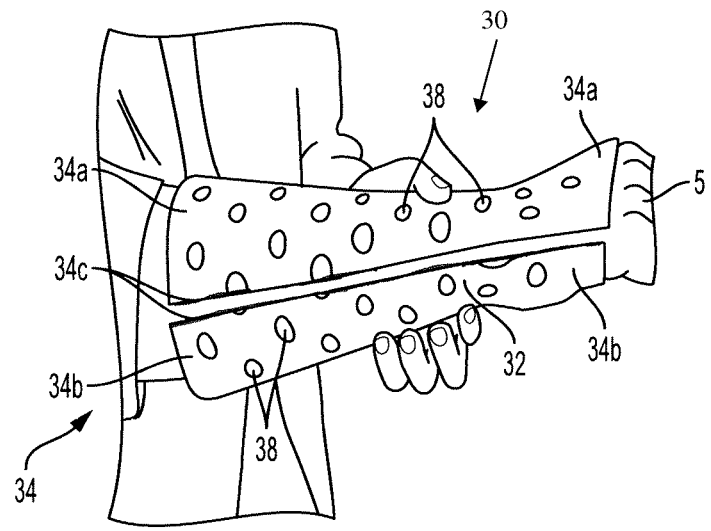
FIG. 3A is a side perspective view of first and second portions of a 3D printed cast in accordance with a third preferred embodiment of the present invention created from the digitized base cast of FIG. 2A, wherein the first and second portions are being mounted to a patient's arm.
Figure 3B:
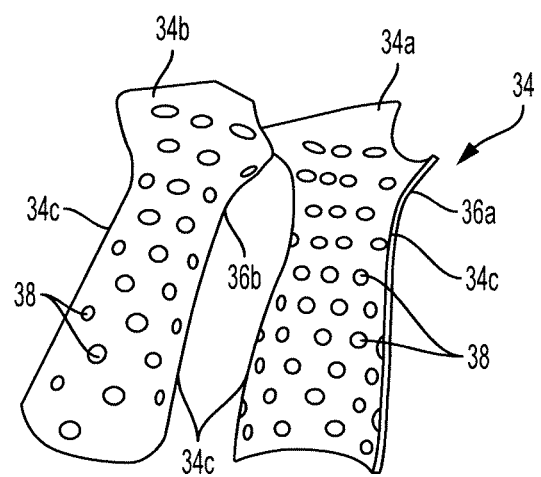
FIG. 3B is a plan view of the first and second portions of the 3D printed cast of FIG. 3A.

Referring to FIGS. 3A and 3B, a third preferred cast or splint 30 has a similar construction compared to the first and second preferred casts or splints 10, 20 and like reference numbers are utilized to identify like features of the third preferred cast or splint 30 with a number "3" prefix replacing the "1" or "2" prefixes, respectively to distinguish the features of the casts or splints 10, 20 of the first and second preferred embodiment from the cast or splint 30 of the third preferred embodiment.

The third preferred cast or splint 30 includes the plurality of venting holes 38 having different sizes and first and second engagement mechanisms 36a, 36b that extend along the entire length of the interfacing edges 34c, respectively. The first and second engagement mechanisms 36a, 36b are preferably comprised of snap-fit or tongue and groove-type engagement mechanisms that secure the first and second shell portions 34a, 34b to each other in the mounted configuration. The first and second shell portions 34a, 34b are preferably snap fit to each other by aligning the interfacing edges 34c and applying pressure toward each other (FIG. 3A) to secure the first and second shell portions 34a, 34b together to define the third preferred cast or splint 30. The engagement mechanisms 36a, 36b may be configured to permit release of the first and second shell portions 34a, 34b after initial engagement or may be designed and configured to permit disengagement and re-engagement so that the third preferred cast or splint 30 may be applied and removed from the body part 5 as desired by the user. These snap-fit or snap-lock first and second engagement mechanisms 36a, 36b are preferably integrally formed with the first and second shell portions 34a, 34b, respectively, but are not so limited and may be separately formed and mounted to the first and second shell portions 34a, 34b. Alternatively, the first and second engagement mechanisms 36a, 36b may be comprised of adhesive bonding that substantially, permanently engages the first and second shell portions 34a, 34b along the interfacing edges 34c in the mounted configuration. The third preferred cast or splint 30 is preferably mounted to the body part 5 during application of the adhesive bonding along the interfacing edges 34c until the cast or splint 30 is cut from the body part 5.

Figure 4A:
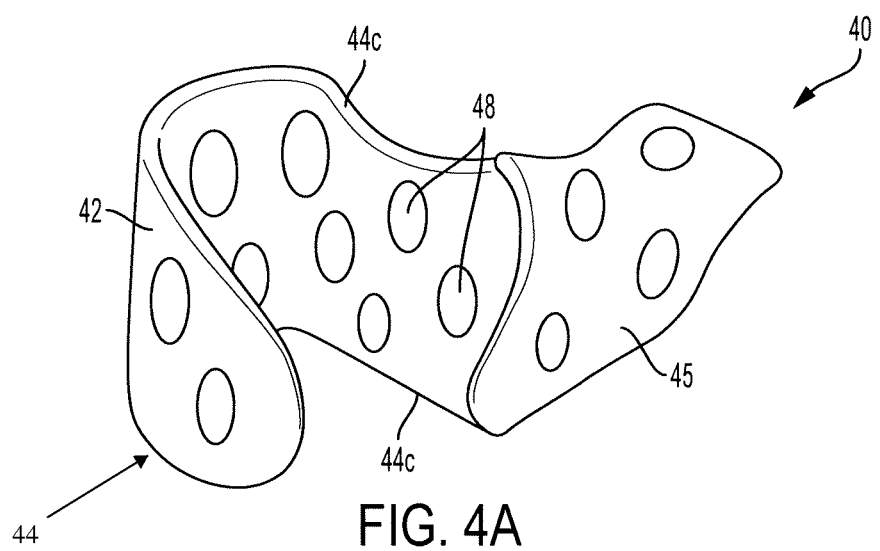
FIG. 4A is a bottom perspective view of a 3D printed base cast in accordance with a fourth preferred embodiment of the present invention created from the digitized base cast of FIG. 2A.
Figure 4B:
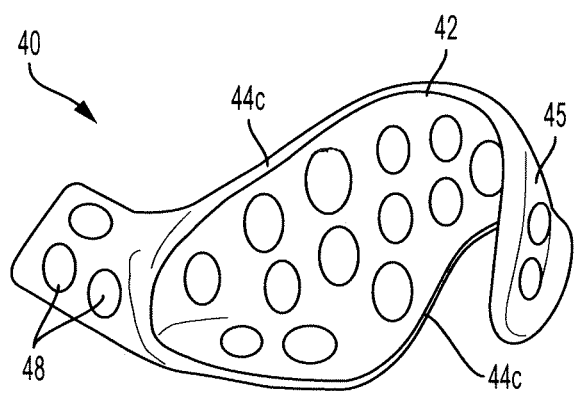
FIG. 4B is a front perspective view of the alternative 3D printed base cast of FIG. 4A.

Referring to FIGS. 4A and 4B, a fourth preferred cast or splint 40 has a similar construction compared to the above-described preferred casts or splints 10, 20, 30 and like reference numbers are utilized to identify like features of the fourth preferred cast or splint 40 with a number "4" prefix replacing the "1," "2" or "3" prefixes, respectively to distinguish the features of the casts or splints 10, 20, 30 of the first, second and third preferred embodiments from the cast or splint 40 of the fourth preferred embodiment.

The fourth preferred cast or splint 40 is comprised of a third shell portion 45 that is configured and 3D printed as a portion of the digitized base cast 14'. The third shell portion 45 is preferably configured as a splint that is releasably removable from the first and second shell portions 14a, 14b, 24a, 24b, 34a, 34b to function as a splint after an initial period of healing utilizing the first, second or third preferred cast or splint 10, 20, 30. In the fourth preferred embodiment, the third shell portion 45 may be utilized with the first and second shell portions 14a, 14b, 24a, 24b, 34a, 34b to initially immobilize the body part 5. The shell portions 14a, 14b, 24a, 24b, 34a, 34b, 45 may then be disassembled after initial healing and the third shell portion 45 may be utilized as a splint to selectively immobilize the joint on a physician prescribed schedule or as desired or required by the patient. In the fourth preferred embodiment, the third shell portion 45 is configured to selectively mount to the patient's thumb and hand, but is not so limited and may be otherwise designed and configured to immobilize other joints. The fourth preferred cast or splint 40 is removably mountable to the first and second shell portions 14a, 14b, 24a, 24b, 34a, 34b along the interfacing edges 44c. The fourth preferred cast or splint 40 may include the coating 42 on the external surfaces, as was described above with respect to the first preferred cast or splint 10.

Figure 5A:
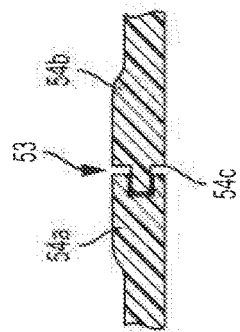
FIG. 5A is a cross-sectional view of a reinforcement portion of the base cast of FIG. 5, taken along line 5A-5A of FIG. 5.
Figure 5:
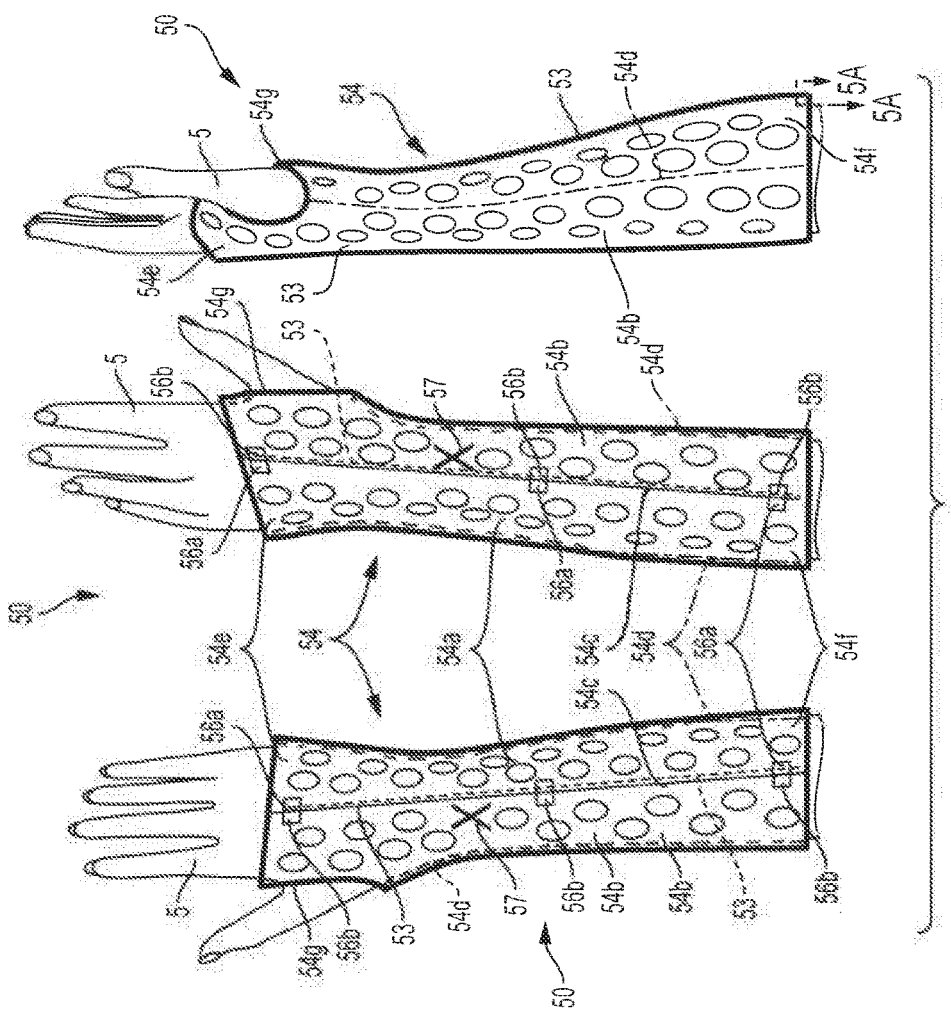
FIG. 5 comprises top and bottom plan views and a side elevational view of a 3D printed base cast in accordance with a fifth preferred embodiment of the present invention created from the digitized base cast of FIG. 2A.

Referring to FIGS. 5 and 5A, a fifth preferred cast or splint 50 has a similar construction compared to the above-described preferred casts or splints 10, 20, 30, 40 and like reference numbers are utilized to identify like features of the fifth preferred cast or splint 50 with a number "5" prefix replacing the "1," "2," "3" or "4" prefixes, respectively to distinguish the features of the casts or splints 10, 20, 30, 40 of the first, second, third and fourth preferred embodiments from the cast or splint 50 of the fifth preferred embodiment.

The fifth preferred cast or splint 50 has a distal end 54e and a proximal end 54f on each of the first and second shell portions 54a, 54b. In the fifth preferred embodiments, the interfacing edged 54c that separate and define surfaces for joining the first and second shell portions 54a, 54b are defined along the back and front or palm side of the patient's hand and arm. The interfacing edges 54c extend between the distal and proximal ends 54e, 54f such that the first and second shell portions are applied generally laterally on to the patient's arm. The fifth preferred cast or splint 50 also includes a reinforcement portion 53 extending between the proximal and distal ends 54f, 54e. The reinforcement portion 53 is located on the palm side of the first and second shell portions 54a, 54b of the fifth preferred embodiment and extends substantially along the length of the interfacing edges 54c on the palm side. The reinforcement portion 53 is an increased stiffness area or zone that assists in immobilizing the patient's hand and wrist. The reinforcement portion 53 is not limited to being positioned as is shown in the fifth preferred embodiment and may be otherwise arranged and positioned based on clinician, physician and medical professional design requirements and patient needs. The reinforcement portion 53 may be comprised of an increased thickness portion of the first and second shell portions 54a, 54b along the interfacing edges 54c that extends between the distal and proximal ends 54e, 54f. The reinforcement portion 53 is preferably formed during the 3D printing process to form the increases thickness portion, which preferably increases strength and stiffness of the base cast 54 along the reinforcement portion 53. The reinforcement portion 53 may alternatively be constructed by printing a stiffer and stronger material along the reinforcement portion 53 than in other portions of the first and second shell portions 54a, 54b or increasing internal architecture (i.e. fill) along the reinforcement zone 53. The reinforcement portion 53 may also be constructed of a separate stiffener rod or bar (not shown) that is selectively and removably mounted to the base cast 54 along the reinforcement zone 53 to provide enhanced strength and stiffness. The reinforcement portion 53 may further be constructed of a substantially solid portion of the base cast 54 wherein none of the venting holes 58 are positioned between the distal and proximal ends 54e, 54f. The separate stiffener or bar may be constructed by the 3D printer with attachment mechanisms formed in the first and second shell portions 54a, 54b for mounting the stiffener or bar to the base cast 54 in the mounted configuration. The placement of the reinforcement portion 53 of the fifth preferred base cast or splint 54 may be utilized to treat the patient's distal radius or ulna, forearm bones, a carpal fracture, a wrist fracture or other similar condition.

The fifth preferred base cast 54 also includes a bone stimulation port 57 formed on the second shell portion 54b. The bone stimulation port 57 is formed during the 3D printing process and is configured to receive a bone stimulator for treatment of the patient's body part 5. The bone stimulation port 57 of the fifth preferred embodiment is comprised of two bone stimulation ports 57 with one positioned on a front portion and one positioned on a back portion of the second shell portion 54b. The bone stimulation ports 57 are positioned near the wrist of the patient in the mounted configuration and may be otherwise positioned or arranged based on the patient's condition or physician requirements. The fifth preferred cast or splint 10 is not limited to inclusion of the bone stimulation port 57 or to the location of the bone stimulation ports 57 of the fifth preferred embodiments. The preferred cast or splint 50 may be constructed without the bone stimulation port 57 and may be configured having the bone stimulation port 57 if nearly any location on the first and second shell portions 54a, 54b. The bone stimulation port 57 is preferably sized and configured for receipt of a physician preferred bone stimulator 57. The fifth preferred cast or splint 50 and the 3D printing process for constructing the cast or splint 50 is particularly adaptable for positioning the bone stimulation port 57 at nearly any location on the cast or splint 50. The bone stimulation port 57 is preferably integrated into the digitized base cast 14' by the designer and printed into the second shell portion 54b. Accordingly, the bone stimulation port 57 can be moved to various locations and quickly produced with the 3D printer 7.

The fifth preferred cast or splint 50 may alternatively be configured as a splint by eliminating the interfacing edges 54c and separating the base cast 54 along splint conversion edges 54d that extend along lateral sides between the distal and proximal ends 54e, 54f of the base cast 54. The cast or splint 50 may also be constructed and placed in the mounted configuration using only a half section of the base cast 54 or mounting only the first or second shell portion 54a, 54b to the body part 5. The base cast 54 configured as a splint using the splint conversion edges 54d preferably includes the reinforcement portion 53 to provide added strength and stiffness. The base cast 54 configured as a splint with the base cast 54 separated along the splint conversion edges 54d is preferably strapped or otherwise secured to the patient's body part 5 to temporarily immobilize the joint of the body part 5.

The fifth preferred base cast 54 is preferably constructed with the distal end 54e extending laterally across the distal palmar crease and the proximal end 54f positioned distally of the elbow on the forearm of the patient. The base case 54 preferably includes a thumb hole 54g formed along the interfacing edges 54c of the first and second shell portions 54a, 54b to accommodate the patient's thumb. This fifth preferred base cast 54 or base cast 54 configured as a splint immobilizes the patient's wrist in the mounted configuration while permitting movement of each of the patient's fingers and the thumb.

Referring to FIG. 6, a sixth preferred cast or splint 60 has a similar construction compared to the above-described preferred casts or splints 10, 20, 30, 40, 50 and like reference numbers are utilized to identify like features of the sixth preferred cast or splint 60 with a number "6" prefix replacing the "1," "2," "3," "4" or "5" prefixes, respectively to distinguish the features of the casts or splints 10, 20, 30, 40, 50 of the first, second, third, fourth and fifth preferred embodiments from the cast or splint 60 of the sixth preferred embodiment.

The sixth preferred base cast 64 includes the interfacing edges 64c and the splint conversion edges 64d positioned along the mid-line of the patient's arm 5 and the distal end 64e extending past the knuckle on the patient's thumb. The reinforcement portion 63 is positioned along the inner edge of the patient's arm extending from the distal end 54e at the thumb to the proximal end 64f. The reinforcement portion 63 is preferably formed exclusively on the first shell portion 64a. The bone stimulation port 67 is also preferably defined on the first shell portion 64a proximate the base of the metacarpal of the thumb in the mounted configuration. The sixth preferred cast or splint 60 is configured to treat scaphoid fractures, carpal bone fractures and conditions related to the radial styloid. When utilized as a splint, the first shell portion 64a may be secured or mounted to the patient's arm 5 with straps by itself to substantially immobilize the thumb. In addition, the bone stimulation port 67 may be otherwise positioned on the first or second shell portions 64a, 64b to promote healing or otherwise stimulate bones or other tissue.

Figure 7:
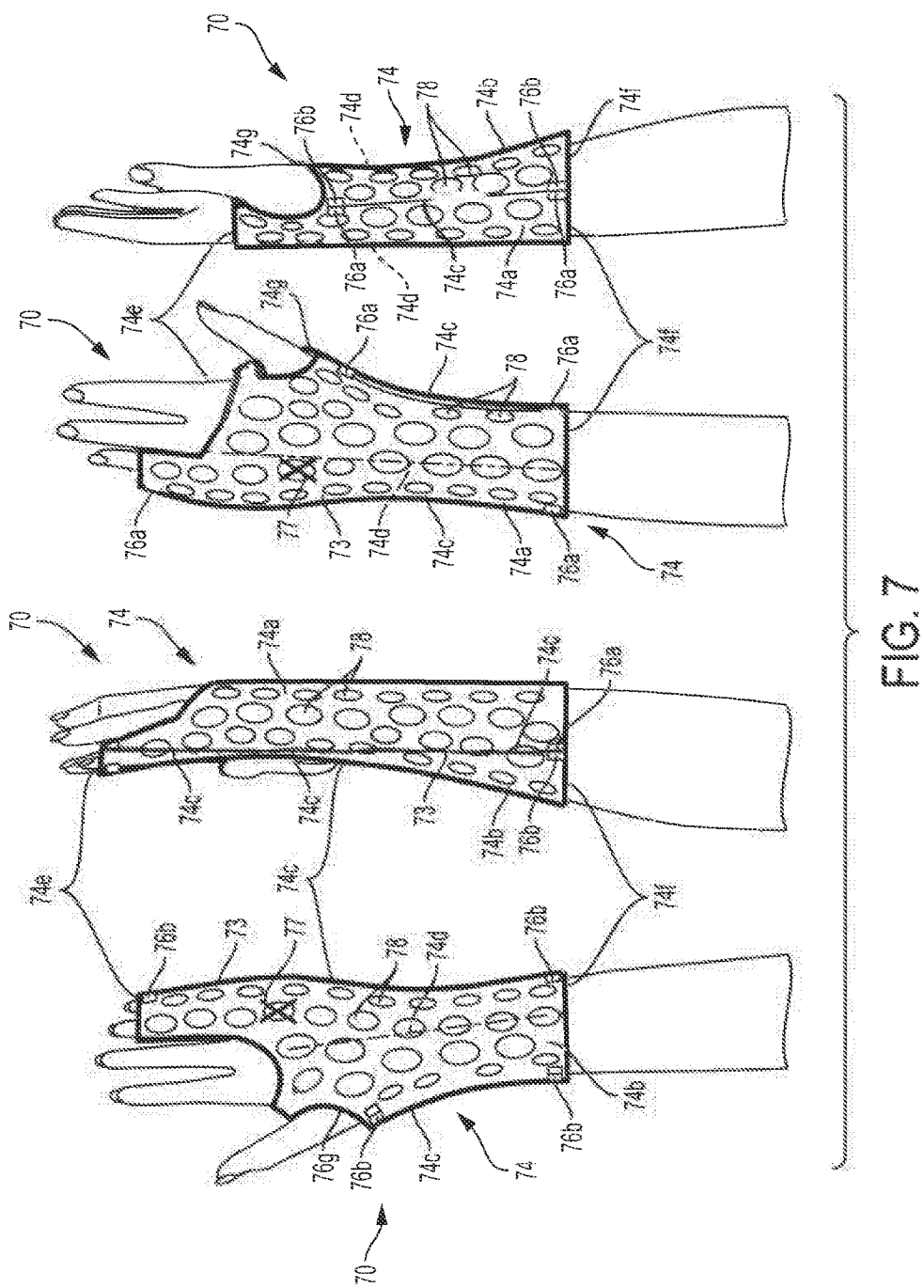
FIG. 7 comprises top and bottom plan views and opposing side elevational views of a 3D printed base cast in accordance with an seventh preferred embodiment of the present invention created from the digitized base cast of FIG. 2A.

Referring to FIG. 7, a seventh preferred cast or splint 70 has a similar construction compared to the above-described preferred casts or splints 10, 20, 30, 40, 50, 60 and like reference numbers are utilized to identify like features of the seventh preferred cast or splint 70 with a number "7" prefix replacing the "1," "2," "3," "4," "5" or "6" prefixes, respectively to distinguish the features of the casts or splints 10, 20, 30, 40, 50, 60 of the first, second, third, fourth, fifth and sixth preferred embodiments from the cast or splint 70 of the seventh preferred embodiment.

The seventh preferred base cast 74 includes the reinforcement portion 73 extending between the proximal and distal ends 74f, 74e along the outer lateral side of the patient's arm to extend along the side of the user's pinky. The distal end 74e of the base cast 74 extends between the distal and middle phalanges of the pinky and ring fingers, across the back of the knuckles of the middle and pointer fingers to the thumb hole 74g and from the knuckle of the thumb to between the proximal phalanges of the middle and ring fingers in the mounted configuration such that the pinky and ring fingers are substantially immobilized, while the thumb, pointer and middle fingers are exposed for movement. The proximal end 74f of the base cast 74 of the seventh preferred embodiment also preferably does not extend as far along the patient's forearm toward the elbow as the proximal ends 54f, 64f of the fifth and sixth preferred embodiments. The seventh preferred base cast 74 is preferably utilized to treat fourth and fifth metacarpal fractures and fourth and fifth proximal and middle phalanges fractures. The bone stimulation port 77 is preferably positioned over the fourth and fifth metacarpals on the first and/or second shell portions 74a, 74b for application of bone stimulation. The splint conversion edges 74d preferably extend along the mid-line of the base cast 74. The base cast 74 of the seventh preferred embodiment is shown with the fourth and fifth digits in a substantially straight position, but the base cast 74 may alternatively be configured such that the fourth and fifth digits are positioned in an intrinsic plus position or nearly any other alternative position desired by the surgeon or medical professional.

Figure 8:
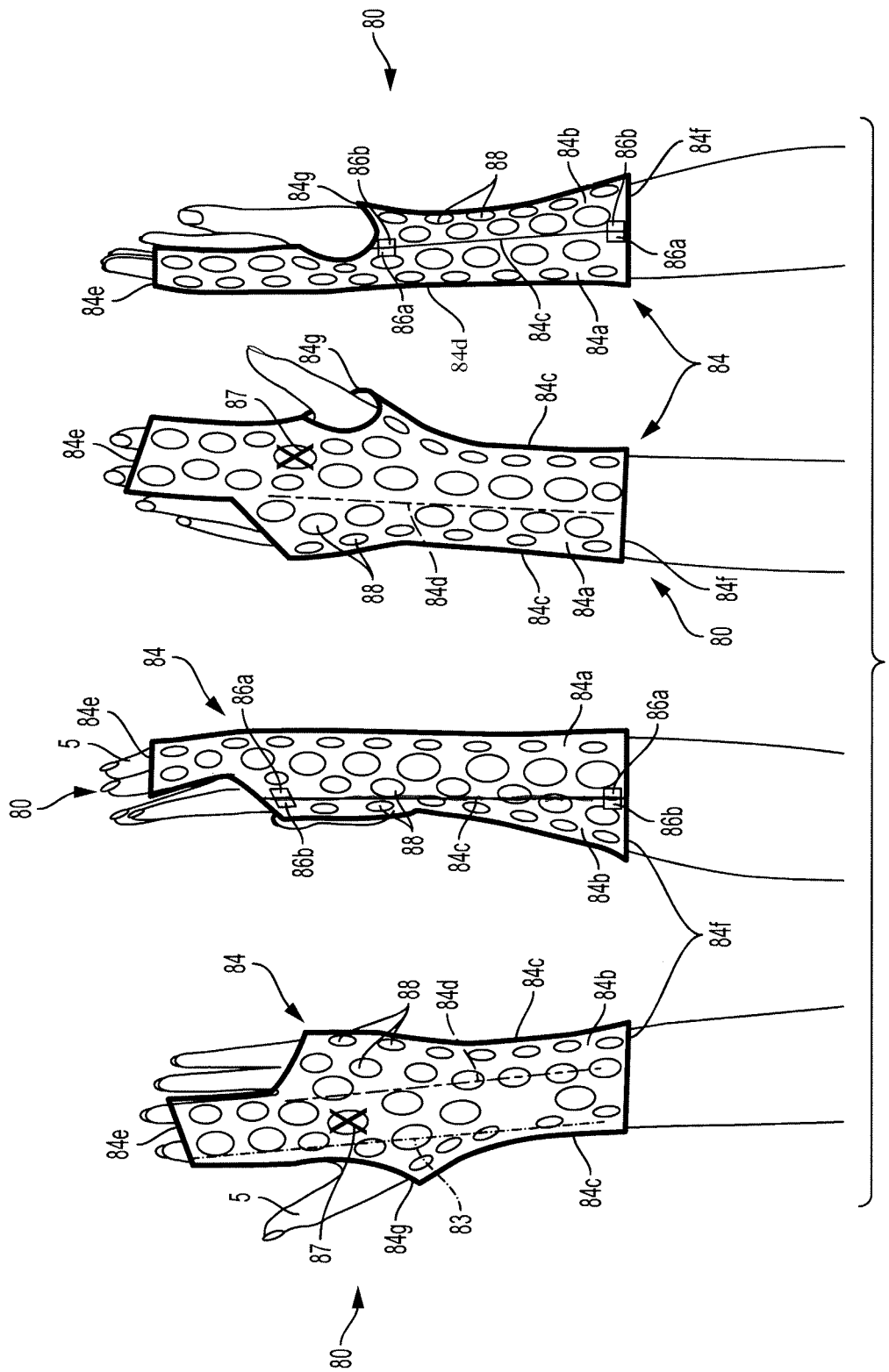
FIG. 8 comprises top and bottom plan views and opposing side elevational views of a 3D printed base cast in accordance with a eighth preferred embodiment of the present invention created from the digitized base cast of FIG. 2A.

Referring to FIG. 8, a eighth preferred cast or splint 80 has a similar construction compared to the above-described preferred casts or splints 10, 20, 30, 40, 50, 60, 70 and like reference numbers are utilized to identify like features of the eighth preferred cast or splint 80 with a number "8" prefix replacing the "1," "2," "3," "4," "5," "6" or "7" prefixes, respectively to distinguish the features of the casts or splints 10, 20, 30, 40, 50, 60, 70 of the first, second, third, fourth, fifth, sixth and seventh preferred embodiments from the cast or splint 80 of the eighth preferred embodiment.

The eighth preferred base cast 84 includes a reinforcement portion that extends substantially longitudinally from the distal end 84e proximate the tips of the pointer and middle fingers or second and third metacarpals to the proximal end 84f on the second shell portion 84b. The distal end 84e extends across the pointer and middle fingers proximate their ends, substantially around the knuckle of the thumb and substantially across the knuckles of the pinky and ring fingers. The bone stimulation port 87 is positioned proximate the second and third metacarpals in the mounted configuration on the first and second shell portions 84a, 84b, but are not so limited and the base cast 84 may include only a single bone stimulation portion 87 on one of the first and second shell portions 84a, 84b or may be constructed without the bone stimulation port 87, without significantly impacting the design and construction of the eighth preferred cast or splint 80. The splint conversion edges 84d preferably extend along a mid-line of the base cast 84 between the distal and proximal ends 84e, 84f. The eighth preferred cast or splint 80 is designed and configured for treatment of second and third metacarpal fractures and other related finger fractures, wherein the second and third metacarpals are substantially immobilized and the thumb and fourth and fifth metacarpals are generally exposed to retain movement in the mounted configuration.

Figure 9:
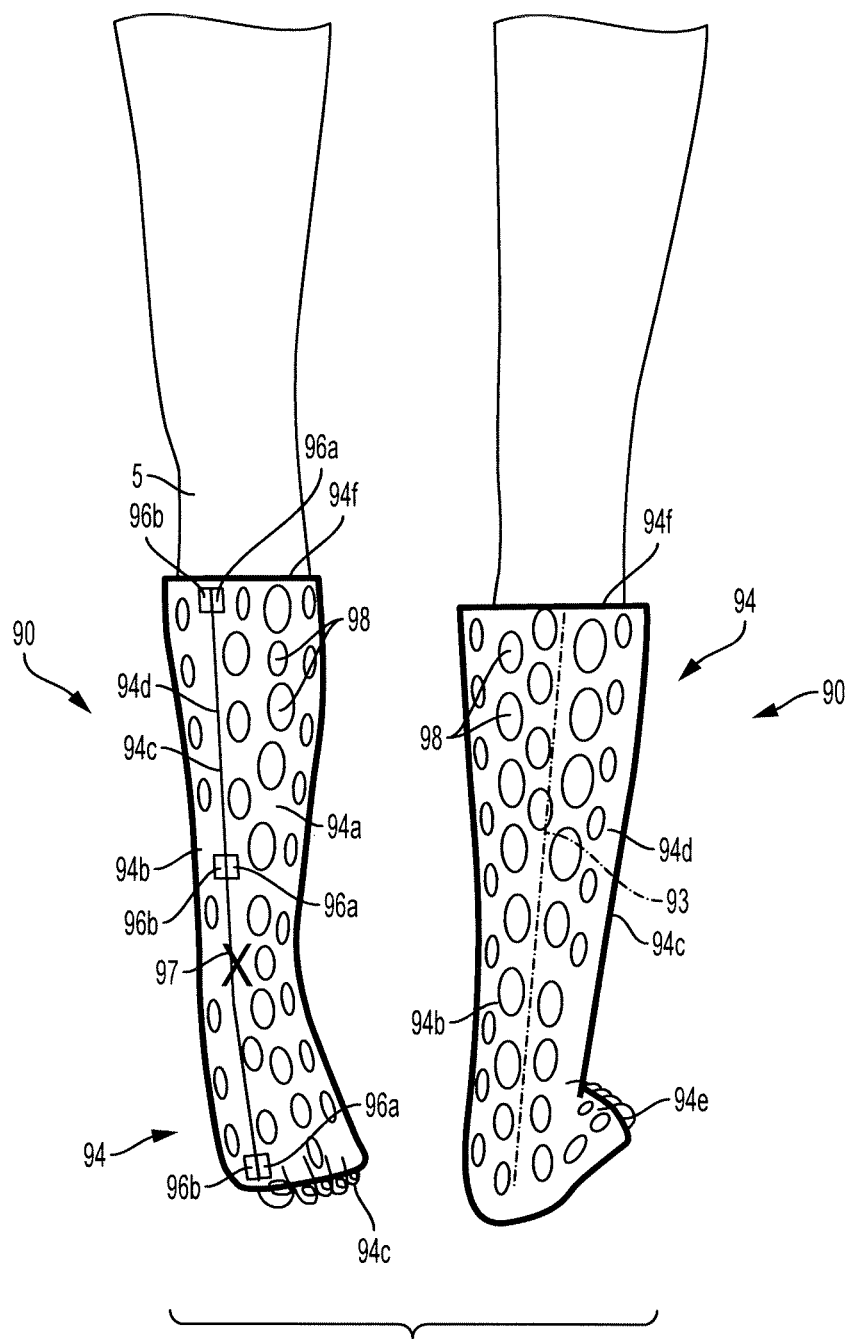
FIG. 9 comprises front and rear perspective views of a 3D printed base cast in accordance with a ninth preferred embodiment of the present invention, wherein the tenth preferred base cast is configured for mounting to a patient's foot, ankle and lower leg.

Referring to FIG. 9, a ninth preferred cast or splint 90 has a similar construction compared to the above-described preferred casts or splints 10, 20, 30, 40, 50, 60, 70, 80 and like reference numbers are utilized to identify like features of the eighth preferred cast or splint 90 with a number "9" prefix replacing the "1," "2," "3," "4," "5," "6," "7" or "8" prefixes, respectively to distinguish the features of the casts or splints 10, 20, 30, 40, 50, 60, 70, 80 of the first, second, third, fourth, fifth, sixth, seventh and eighth preferred embodiments from the cast or splint 90 of the ninth preferred embodiment.

The ninth preferred cast or splint 90 is specifically designed for treatment of the patient's lower leg, ankle and foot 5. The interfacing edges 94c and splint conversion edges 94d preferably extend along lateral sides of the patient's leg and foot in the mounted configuration and the reinforcement portion extends from the proximal end 94f to the bottom of the base cast 94, as is shown in FIG. 9. The ninth preferred cast or splint 90 may be constructed of a stronger and stiffer material than the first through eighth preferred casts or splints 10, 20, 30, 40, 50, 60, 70, 80 to bear the greater forces encountered by the base cast 94 of the ninth preferred embodiment.

The base casts 14, 24, 34, 44, 54, 64, 74, 84, 94 of the first through ninth preferred embodiment may each include the coating 12, 22, 32, 42, 52, 62, 72, 82, 92 on external surfaces. The coating 12, 22, 32, 42, 52, 62, 72, 82, 92 may be applied after 3D printing of the base casts 14, 24, 34, 44, 54, 64, 74, 84, 94 of may be printed thereon with the 3D printer 7. The base casts 14, 24, 34, 44, 54, 64, 74, 84, 94 may also include flexible skins (now shown) or paddings for ornamental or safety purposes. The flexible skins may have a skin color, advertisement, logo, or other ornamental designs thereon to cover and protect the base casts 14, 24, 34, 44, 54, 64, 74, 84, 94 and/or to provide a preferred ornamental appearance. The flexible skins may slide over the casts 14, 24, 34, 44, 54, 64, 74, 84, 94 and be retained thereon as a result of their own flexibility or may be fastened, clipped, adhesively bonded or otherwise secured to the preferred casts 14, 24, 34, 44, 54, 64, 74, 84, 94. The flexible skin may be constructed of nearly any substantially flexile material that may be sized and shaped to fit over the base casts 14, 24, 34, 44, 54, 64, 74, 84, 94, withstand the normal operating conditions of the flexible skin and perform the normal operating conditions of the flexible skin, such as spandex, nylon, fabrics or other related materials. The base casts 14, 24, 34, 44, 54, 64, 74, 84, 94 may include the padding for safety of the patient or others and may be padded for sports participation. The base casts 14, 24, 34, 44, 54, 64, 74, 84, 94 may further include hollow portions or lumens therethrough that receive flow of cooling fluid or other therapeutic fluid for treatment of swelling, bone stimulation, burns, skin irritation or other purposes. The flow of the fluid may be controlled by pumps and a control mechanism (not shown) associated with the base casts 14, 24, 34, 44, 54, 64, 74, 84, 94 or may be manually actuated by the patient or a medical professional. The flow of cooling or therapy fluids or medications may be applied to the entire base cast 14, 24, 34, 44, 54, 64, 74, 84, 94 or may be focused on a target area, such as an area adjacent the bone stimulation port 57, 67, 77, 87, 97. The base casts 14, 24, 34, 44, 54, 64, 74, 84, 94 may further be configured with exit holes from the hollow portions or lumens that dispense medication onto the body part 5, such as antibiotics, antiseptics, cleaning fluids or other materials utilized for treatment of the body part 5. In this configuration, the base casts 14, 24, 34, 44, 54, 64, 74, 84, 94 preferably include a built-in reservoir for the medication and a dosing mechanism that permits automatic or manual dosing of the medication at predetermined time periods or as required.

Swelling may occur to the body part 5 following an injury or surgery, making scanning with the visual digitization mechanism 3 and creation of the digitized base cast 14' difficult and inaccurate. Where the physician, technician or visual digitization mechanism 3 detects significant swelling of the body part 5 that may impact the accuracy of the digitized base cast 14', the opposing or contralateral body part 5 may be scanned using the visual digitization mechanism 3 and the digitized base cast 14' may be electrically manipulated to create a mirror image of the digitized base cast 14' for application to the impacted body part 5 once the swelling dissipates. Swelling may alternatively be addressed by the ratcheting-type first and second engagement mechanisms 16a, 16b, 26a, 36a, 36b, 56a, 56b, 66a, 66b, 76a, 76b, 86a, 86b, 96a, 96b, as was described above.

The bone stimulation ports 57, 67, 77, 87, 97 may also be adapted to accept a wear chip (not shown) that is permanently or releasably attached to the base cast 54, 64, 74, 84, 94 for tracking movement, temperature, blood pressure, stress, strain, pressure, time worn, blood oxygenation or other data that may be detected by sensors associated with the wear chip. The wear chip may also be configured to receive subjective data from the patient or a medical professional, such as pain levels, comfort levels, satisfaction or other related subjective patient data. The wear chip preferably includes a wireless or wired transmitter that transmits the collected data to a central processor for review and consideration by a care giver. The wear chip may further include a waring indicator, such as an audible alarm, a visual alarm, vibration or other detectable alarm to provide reminders to the user related to treatment or therapy. For example, the wear chip may provide an auditory alarm to the patient indicating the patient has not moved for an extended period of time, to prompt the user to perform physical therapy or otherwise move or apply pressure to the impacted body part 5. The wear chip may, for example, also provide a vibratory warning or alarm based on the elevational position of the base cast 54, 64, 74, 84, 94 to remind the patient to elevate the base cast 54, 64, 74, 84, 94 and the body part 5 to reduce swelling, promote blood flow or otherwise provide therapy to the body part 5. The wear chip may alternatively, for example, include a weight bearing sensor, particularly for the base cast 94 of the ninth preferred embodiment to provide information to the care giver related to whether the patient is walking, following therapy routines or overstressing the body part 5. The wear chip may further be associated with a pressure sensor that is able to detect pressure exerted on the base cast 54, 64, 74, 84, 94 from the body part, potentially indicating excessive swelling of the body part 5 and provide a warning to the patient to seek medical attention, loosen the base cast 54, 64, 74, 84, 94, remove the base cast 54, 64, 74, 84, 94 or otherwise address the excessive pressure or swelling situation. The wear chip may send a signal to a central server or controller that is able to direct printing of a larger base cast 54, 64, 74, 84, 94 to accommodate the swelling or excessive pressure with the 3D printer 7. The wear chip may further detect localized pressures or pressure points between the base cast 54, 64, 74, 84, 94 and the body part 5 and send a signal to the central server to print a replacement base cast 54, 64, 74, 84, 94 that provides additional spacing or other relief to address the localized excessive pressure or pressure that exceeds a predetermined threshold. The wear chip may also include storage capability for maintenance of the patient's electronic medical records ("EMR"), collected data from sensors, therapy protocols for the patient or other information associated with the patient, the patient's condition or the base casts 14, 24, 34, 44, 54, 64, 74, 84, 94. The wear chip may also include an emergency indicator that can be actuated by the patient for wireless communication with a central server or emergency services to solicit assistance or emergency assistance for the patient, as required.

The preferred base casts 14, 24, 34, 44, 54, 64, 74, 84, 94 include a fill ratio related to the material of the base casts 14, 24, 34, 44, 54, 64, 74, 84, 94 related to the solid portion of material versus internal voids in the material. The fill ratio of the base casts of the preferred embodiments is generally about fifty to seventy percent (50-70%) with the solid portion of the material comprising the greater amount of the base casts 14, 24, 34, 44, 54, 64, 74, 84, 94 when compared to the voids. The base casts 14, 24, 34, 44, 54, 64, 74, 84, 94 are not limited to such fill ratios and may be constructed with a one hundred percent fill ratio or nearly one hundred percent. The preferred casts or splints 10, 20, 30, 40, 50, 60, 70, 80, 90 also preferably have a vent hole density comprised of the amount of volume of the base cast 14, 24, 34, 44, 54, 64, 74, 84, 94 occupied by the material of the base casts 14, 24, 34, 44, 54, 64, 74, 84, 94 versus the amount of space taken by the vent holes 18, 28, 38, 48, 58, 68, 78, 88, 98. The vent hole density of the base cast 14, 24, 34, 44, 54, 64, 74, 84, 94 is preferably approximately fifty to seventy percent (40-70%) with the material of the base casts 14, 24, 34, 44, 54, 64, 74, 84, 94 typically comprising the greater volume. The fill ratio and vent hole density are preferably configured for structural strength and stability of the base casts 14, 24, 34, 44, 54, 64, 74, 84, 94, stability, particular injury being addressed, medical professional preferences and related factors.

The preferred base casts 14, 24, 34, 44, 54, 64, 74, 84, 94 may also be printed with additional features that assist the patient. The additional features may include a prosthetic attachment, tool attachment, utensil attachment, physical therapy attachment, storage pockets or other features. For example, the base casts 14, 24, 34, 44, 54, 64, 74, 84, 94 may have modular configurations, wherein structure proximate the patient's fingers may be temporarily removed for the patient to perform physical therapy with the fingers and the structure re-attached to the remainder of the modular base cast 14, 24, 34, 44, 54, 64, 74, 84, 94 to immobilize the fingers for continued immobilization. The base cast 14, 24, 34, 44, 54, 64, 74, 84, 94 may also be printed with a universal cuff design to allow for adapted utensils/tools for patient's without fine motor control/us so that the patient is able to manipulate tools and/or utensils. The base cast 14, 24, 34, 44, 54, 64, 74, 84, 94 may further be printed with a thumb Spica for holding a fork/spoon/knife for individuals with spinal cord injuries who lack use of their digits for functional feeding. The base cast 14, 24, 34, 44, 54, 64, 74, 84, 94 may include attachments that allow for moving and exercising appendages, such as the fingers, arm, toes and leg, that may include or incorporate rings, elastic bands, hooks, strings attached to resistance mechanisms, resistance balls and other related therapy features.

It will be appreciated by those skilled in the art that changes could be made to the embodiments described above without departing from the broad inventive concept thereof. For example, features and configurations of the preferred casts or splints 10, 20, 30, 40, 50, 60, 70, 80, 90 can be mixed and matched between the embodiments and added to one embodiment from another without significantly impacting the construction and operation of the devices, such as including the symbol 18*a* on any of the embodiments or making portions of the preferred embodiments of the base casts 14, 24, 34, 44, 54, 64, 74, 84, 94 modular, for example, by incorporating the forth preferred base cast 44 as a modular portion of other preferred embodiments. It is understood, therefore, that this invention is not limited to the particular embodiments disclosed, but it is intended to cover modifications within the spirit and scope of the present invention as defined by the present disclosure and the appended claims.

We claim:

1. A 3D printed cast or splint for application to a patient's body to immobilize a body part of the patient's body, the cast or splint comprising:
    a first shell portion constructed of a substantially rigid polymeric material and having a distal end, a proximal end and opposing interfacing edges, the first shell portion includes a plurality of venting holes that expose the patient's skin, a first engagement mechanism positioned proximate one of the opposing interfacing edges and a reinforcement portion extending between the proximal and distal ends, the reinforcement portion positioned generally along a mid-line between the opposing interfacing edges, at least one of the plurality of venting holes positioned between the reinforcement portion and the opposing interfacing edges, the reinforcement portion comprised of a substantially solid portion of the first shell wherein none of the plurality of venting holes are positioned between the proximal and distal ends, wherein the reinforcement portion is comprised of an increased thickness portion compared to a thickness of other portions of the first shell extending from the distal end to the proximal end of the first shell portion, the first shell portion including a flex area proximate a wrist portion of the first shell; and
    a second shell portion constructed of the substantially rigid polymeric material and having a distal end, a proximal end and opposing interfacing edges, the second shell portion includes a plurality of venting holes and a second engagement mechanism positioned proximate one of the opposing interfacing edges of the second shell portion, the first and second shell portions configured to conform to at least a portion of the body part, the first engagement mechanism interacting with the second engagement mechanism in a mounted configuration to facilitate mounting of the first shell portion to the second shell portion, the interfacing edges of the first shell portion positioned adjacent the interfacing edges of the second shell portion in the mounted configuration.

2. The 3D printed cast or splint of claim 1, further comprising:
an inert polymeric coating adhered to external surfaces of the first and second shell portions.

3. The 3D printed cast or splint of claim 1, wherein the polymeric material is comprised of a composite carbon material.

4. The 3D printed cast or splint of claim 1, wherein the first shell portion includes a bone stimulation port.

5. The 3D printed cast or splint of claim 1, wherein the first engagement mechanism is comprised of a first boss and the second engagement mechanism comprised of a second boss, the first boss positioned in facing engagement with the second boss in the mounted configuration.

6. The 3D printed cast or splint of claim 1, wherein the venting holes are formed in a shape of a symbol.

7. The 3D printed cast or splint of claim 6, wherein the symbol is a corporate logo.

8. The 3D printed cast or splint of claim 1, wherein the proximal ends of the first and second shells are configured for positioning adjacent the patient's forearm and at least a section of the distal ends of the first and second shells are configured for positioning adjacent the patient's palmar crease in the mounted configuration.

9. The 3D printed cast or splint of claim 1, wherein the venting holes have various shapes and sizes.

10. The 3D printed cast or splint of claim 1, wherein the polymeric material is comprised of a material selected from the group consisting of polycarbonate, polyether ether ketone ("PEEK"), a powder polymeric material, acrylonitrile butadiene styrene ("ABS"), polylactic acid ("PLA"), a biocompatible thermoplastic, nylon, a synthetic polymer, aliphatic polyamides, semi-aromatic polyamides and carbon reinforced composite.

11. The 3D printed cast or splint of claim 1, wherein the first engagement mechanism is integrally formed in the first shell portion and the second engagement mechanism is integrally formed in the second shell portion.

12. The 3D printed cast or splint of claim 1, wherein the first and second engagement mechanisms include a locking mechanism, the locking mechanism configured to provide a visual indication if the locking mechanism has been at least one of opened and tampered with after being locked together, the visual indication comprised of the locking mechanism changing colors.

* * * * *